United States Patent
Nyemscek et al.

(10) Patent No.: US 10,792,397 B2
(45) Date of Patent: Oct. 6, 2020

(54) BIOACTIVE BONE GRAFT SUBSTITUTES

(71) Applicant: GLOBUS MEDICAL, INC., Audubon, PA (US)

(72) Inventors: Jevon Nyemscek, Brookhaven, PA (US); Vipin Kunjachan, Norristown, PA (US); Allison Adams, Conshohocken, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 16/218,630

(22) Filed: Dec. 13, 2018

(65) Prior Publication Data

US 2019/0117842 A1    Apr. 25, 2019

Related U.S. Application Data

(63) Continuation of application No. 13/493,531, filed on Jun. 11, 2012, now Pat. No. 10,207,027.

(51) Int. Cl.
| | | |
|---|---|---|
| *A61L 27/44* | (2006.01) | |
| *A61L 27/38* | (2006.01) | |
| *A61L 27/50* | (2006.01) | |
| *A61L 27/56* | (2006.01) | |
| *A61L 24/00* | (2006.01) | |
| *A61L 27/54* | (2006.01) | |

(52) U.S. Cl.
CPC ........... *A61L 27/446* (2013.01); *A61L 24/001* (2013.01); *A61L 24/0005* (2013.01); *A61L 24/0015* (2013.01); *A61L 24/0036* (2013.01); *A61L 24/0089* (2013.01); *A61L 27/3804* (2013.01); *A61L 27/50* (2013.01); *A61L 27/54* (2013.01); *A61L 27/56* (2013.01); *A61L 2300/412* (2013.01); *A61L 2430/02* (2013.01)

(58) Field of Classification Search
CPC ............................ A61L 24/0036; A61L 27/446
See application file for complete search history.

(56) References Cited

U.S. PATENT DOCUMENTS

| | | |
|---|---|---|
| 4,437,191 A | 3/1984 | van der Zel et al. |
| 5,681,872 A | 10/1997 | Erbe |
| 5,700,289 A | 12/1997 | Breitbart et al. |
| 5,776,193 A | 7/1998 | Kwan et al. |
| 5,854,207 A | 12/1998 | Lee et al. |
| 5,914,356 A | 6/1999 | Erbe |
| 5,939,039 A | 8/1999 | Sapieszko et al. |
| 5,977,204 A | 11/1999 | Boyen et al. |
| 6,123,731 A | 9/2000 | Boyce et al. |
| 6,264,701 B1 | 7/2001 | Brekke |
| 6,294,041 B1 | 9/2001 | Boyce et al. |
| 6,309,659 B1 | 10/2001 | Clokie |
| 6,350,283 B1 | 2/2002 | Michelson |
| 6,372,257 B1 | 4/2002 | Marchosky |
| 6,432,436 B1 | 8/2002 | Gertzman et al. |
| 6,437,018 B1 | 8/2002 | Gertzman et al. |
| 6,666,890 B2 | 12/2003 | Michelson |
| 6,696,073 B2 | 2/2004 | Boyce et al. |
| 6,706,067 B2 | 3/2004 | Shimp et al. |
| 6,723,131 B2 | 4/2004 | Muschler |
| 6,749,636 B2 | 6/2004 | Michelson |
| 6,752,831 B2 | 6/2004 | Sybert et al. |
| 6,776,800 B2 | 8/2004 | Boyer, II et al. |
| 6,808,585 B2 | 10/2004 | Boyce et al. |
| 6,843,807 B1 | 1/2005 | Boyce et al. |
| 6,919,308 B2 | 7/2005 | Oppermann et al. |
| 6,926,903 B2 | 8/2005 | Pirhonen et al. |
| 6,949,251 B2 | 9/2005 | Dalal et al. |
| 7,022,137 B2 | 4/2006 | Michelson |
| 7,041,641 B2 | 5/2006 | Rueger et al. |
| 7,132,110 B2 | 11/2006 | Kay et al. |
| 7,156,880 B2 | 1/2007 | Evans et al. |
| 7,166,133 B2 | 1/2007 | Evans et al. |
| 7,175,858 B2 | 2/2007 | Constantz et al. |
| 7,235,107 B2 | 6/2007 | Evans et al. |
| 7,262,003 B2 | 8/2007 | Kumar et al. |
| 7,275,933 B2 | 10/2007 | Jia et al. |
| 7,291,345 B2 | 11/2007 | Winterbottom et al. |
| 7,332,452 B2 | 2/2008 | Ogawa et al. |

(Continued)

FOREIGN PATENT DOCUMENTS

| | | |
|---|---|---|
| AU | 2004242432 A1 | 1/2005 |
| CA | 1341610 C | 4/1989 |

(Continued)

OTHER PUBLICATIONS

Sun et al., "Dextran hydrogel scaffolds enhance angiogenic responses and promote complete skin regeneration during burn wound healing", Applied Biological Sciences, PNAS, vol. 108, No. 52, 6 pages, Dec. 27, 2011.

*Primary Examiner* — Kyle A Purdy

(57) ABSTRACT

Provided are synthetic bone graft substitutes that include bioactive glass and a carrier. Synthetic bone graft substitutes may include bioactive glass, glycerol and polyethylene glycol. Also provided are bone graft substitutes that include collagen and bioactive glass particles. Example bone graft substitutes may include collagen and bioactive glass particles. Other example embodiments may include Type I Bovine Collagen, an angiogenic agent, such as hyaluronic acid, and bioactive glass. Further provided are methods that include administering the present bone graft substitutes to a mammal, e.g., by surgical insertion of the bone graft substitute into the mammal, either alone or in conjunction with one or more implant devices. Further provided are kits that include the present bone grafts.

18 Claims, 1 Drawing Sheet

(56) References Cited

U.S. PATENT DOCUMENTS

| | | |
|---|---|---|
| 7,390,498 B2 | 6/2008 | Dalal et al. |
| 7,393,405 B2 | 7/2008 | Bohner |
| 7,473,678 B2 | 1/2009 | Lynch |
| 7,494,950 B2 | 2/2009 | Armitage et al. |
| 7,498,041 B2 | 3/2009 | Masinaei et al. |
| 7,517,489 B2 | 4/2009 | Akash |
| 7,582,309 B2 | 9/2009 | Rosenberg et al. |
| 7,611,536 B2 | 11/2009 | Michelson |
| 7,723,395 B2 | 5/2010 | Ringeisen et al. |
| 7,744,597 B2 | 6/2010 | Gaskins et al. |
| 7,776,100 B2 | 8/2010 | Brekke et al. |
| 7,785,634 B2 | 8/2010 | Borden |
| 7,811,608 B2 | 10/2010 | Kay et al. |
| 7,824,702 B2 | 11/2010 | Wironen et al. |
| 7,833,278 B2 | 11/2010 | Evans et al. |
| 7,887,598 B2 | 2/2011 | Evans et al. |
| 7,892,291 B2 | 2/2011 | Evans et al. |
| 7,910,690 B2 | 3/2011 | Ringeisen et al. |
| 7,931,692 B2 | 4/2011 | Sybert et al. |
| 7,939,108 B2 | 5/2011 | Morris et al. |
| 7,942,961 B2 | 5/2011 | Asgarg |
| 7,947,759 B2 | 5/2011 | Lin et al. |
| 7,959,941 B2 | 6/2011 | Knaack et al. |
| 7,977,094 B2 | 7/2011 | Masinaei et al. |
| 8,002,813 B2 | 8/2011 | Scarborough et al. |
| 8,067,078 B1 | 11/2011 | Espinosa et al. |
| 8,093,313 B2 | 1/2012 | Miller |
| 8,105,383 B2 | 1/2012 | Michelson |
| 8,137,403 B2 | 3/2012 | Michelson |
| 8,147,860 B2 | 4/2012 | Rosenberg et al. |
| 8,147,862 B2 | 4/2012 | McKay |
| 8,163,032 B2 | 4/2012 | Evans et al. |
| 8,188,229 B2 | 5/2012 | Ringeison et al. |
| 8,197,474 B2 | 6/2012 | Scarborough et al. |
| 8,202,539 B2 | 6/2012 | Behnam et al. |
| 8,221,781 B2 | 7/2012 | Rosenberg et al. |
| 8,232,327 B2 | 7/2012 | Garigapati et al. |
| 8,268,008 B2 | 9/2012 | Betz et al. |
| 8,287,915 B2 | 10/2012 | Clineff et al. |
| 8,303,967 B2 | 11/2012 | Clineff et al. |
| 8,303,971 B2 | 11/2012 | Cieslik et al. |
| 8,309,106 B2 | 11/2012 | Masinaei et al. |
| 8,323,700 B2 | 12/2012 | Morris et al. |
| 8,328,876 B2 | 12/2012 | Behnam et al. |
| 8,333,985 B2 | 12/2012 | Knaack et al. |
| 8,357,384 B2 | 1/2013 | Behnam et al. |
| 8,394,141 B2 | 3/2013 | Mills et al. |
| 8,399,409 B2 | 3/2013 | Lynch et al. |
| 8,419,802 B2 | 4/2013 | Evans et al. |
| 8,425,619 B2 | 4/2013 | Evans et al. |
| 8,435,306 B2 | 5/2013 | Evans et al. |
| 8,435,343 B2 | 5/2013 | Yahav et al. |
| 8,435,566 B2 | 5/2013 | Behnam et al. |
| 8,454,988 B2 | 6/2013 | Rosenberg et al. |
| 8,460,686 B2 | 6/2013 | Clineff et al. |
| 8,475,824 B2 | 7/2013 | McKay |
| 8,506,981 B1 | 8/2013 | Borden |
| 8,506,985 B2 | 8/2013 | Garcia De Castro Andrews et al. |
| 8,524,265 B2 | 9/2013 | McKay |
| 8,529,962 B2 | 9/2013 | Morris et al. |
| 8,545,858 B2 | 10/2013 | Rosenberg et al. |
| 8,545,864 B2 | 10/2013 | Morris et al. |
| 8,551,519 B2 | 10/2013 | Bezwada |
| 8,551,525 B2 | 10/2013 | Cook et al. |
| 8,562,648 B2 | 10/2013 | Kaes et al. |
| 8,580,865 B2 | 11/2013 | Peters et al. |
| 8,597,675 B2 | 12/2013 | Murphy et al. |
| 8,613,938 B2 | 12/2013 | Akella et al. |
| 8,623,094 B2 | 1/2014 | Evans et al. |
| 8,641,774 B2 | 2/2014 | Rahaman et al. |
| 8,642,061 B2 | 2/2014 | Shimp et al. |
| 8,652,503 B2 | 2/2014 | Wironen et al. |
| 8,663,326 B2 | 3/2014 | Osman |
| 8,663,672 B2 | 3/2014 | Manrique et al. |
| 8,663,677 B2 | 3/2014 | Fu et al. |
| 8,685,429 B2 | 4/2014 | Koblish et al. |
| 8,734,525 B2 | 5/2014 | Behnam et al. |
| 8,740,987 B2 | 6/2014 | Geremakis et al. |
| 8,747,899 B2 | 6/2014 | Chaput et al. |
| 8,753,391 B2 | 6/2014 | Lu et al. |
| 8,753,689 B2 | 6/2014 | Morris et al. |
| 8,758,792 B2 | 6/2014 | Behnam et al. |
| 8,778,378 B2 | 7/2014 | Clineff et al. |
| 8,795,382 B2 | 8/2014 | Lin et al. |
| 8,802,626 B2 | 8/2014 | Rueger et al. |
| 8,834,928 B1 | 9/2014 | Truncale et al. |
| 8,864,843 B2 | 10/2014 | Lu et al. |
| 8,871,235 B2 | 10/2014 | Borden |
| 8,876,532 B2 | 11/2014 | Atkinson et al. |
| 8,877,221 B2 | 11/2014 | McKay |
| 8,883,210 B1 | 11/2014 | Truncale et al. |
| 8,926,710 B2 | 1/2015 | McKay |
| 8,992,964 B2 | 3/2015 | Shelby et al. |
| 8,992,965 B2 | 3/2015 | Behnam |
| 2001/0038848 A1 | 11/2001 | Donda et al. |
| 2002/0076429 A1 | 6/2002 | Wironen et al. |
| 2002/0098222 A1 | 7/2002 | Wironen et al. |
| 2002/0160032 A1 | 10/2002 | Long et al. |
| 2002/0193883 A1 | 12/2002 | Wironen |
| 2003/0009235 A1 | 1/2003 | Manrique et al. |
| 2003/0055512 A1 | 3/2003 | Genin et al. |
| 2003/0149437 A1 | 8/2003 | Livne et al. |
| 2004/0091462 A1 | 5/2004 | Lin et al. |
| 2005/0118230 A1 | 6/2005 | Hill et al. |
| 2005/0251267 A1 | 11/2005 | Winterbottom et al. |
| 2005/0281856 A1 | 12/2005 | McGlohom et al. |
| 2006/0018942 A1 | 1/2006 | Rowe et al. |
| 2006/0036331 A1 | 2/2006 | Lu et al. |
| 2006/0147545 A1 | 7/2006 | Scarborough et al. |
| 2007/0026030 A1 | 2/2007 | Gill et al. |
| 2007/0083270 A1 | 4/2007 | Masinaei et al. |
| 2007/0098756 A1 | 5/2007 | Behnam |
| 2007/0105222 A1 | 5/2007 | Wolfinbarger et al. |
| 2007/0113951 A1 | 5/2007 | Huang |
| 2007/0202190 A1 | 8/2007 | Borden |
| 2008/0033572 A1 | 2/2008 | D'Antonio et al. |
| 2008/0069852 A1 | 3/2008 | Shimp et al. |
| 2008/0091270 A1 | 4/2008 | Miller et al. |
| 2008/0187571 A1 | 8/2008 | Clineff et al. |
| 2008/0206297 A1 | 8/2008 | Roeder et al. |
| 2008/0226688 A1 | 9/2008 | Depaula |
| 2009/0012625 A1 | 1/2009 | Ying et al. |
| 2009/0074753 A1 | 3/2009 | Lynch |
| 2009/0157087 A1 | 6/2009 | Wei et al. |
| 2009/0192474 A1 | 7/2009 | Wei et al. |
| 2009/0238853 A1 | 9/2009 | Liu |
| 2009/0312842 A1 | 12/2009 | Bursac et al. |
| 2009/0317447 A1 | 12/2009 | Hsiao et al. |
| 2009/0318982 A1 | 12/2009 | Genin et al. |
| 2010/0055078 A1 | 3/2010 | Hughes-Fulford |
| 2010/0119577 A1 | 5/2010 | Min |
| 2010/0145469 A1 | 6/2010 | Barralet et al. |
| 2010/0196333 A1 | 8/2010 | Gaskins et al. |
| 2010/0203155 A1 | 8/2010 | Wei et al. |
| 2010/0234966 A1 | 9/2010 | Lo |
| 2010/0262258 A1 | 10/2010 | Gibson et al. |
| 2011/0045044 A1 | 2/2011 | Masinaei et al. |
| 2011/0066242 A1 | 3/2011 | Lu et al. |
| 2011/0070312 A1 | 3/2011 | Wei et al. |
| 2011/0117018 A1 | 5/2011 | Hart et al. |
| 2011/0117165 A1 | 5/2011 | Melican et al. |
| 2011/0117166 A1 | 5/2011 | Melican |
| 2011/0117171 A1 | 5/2011 | Melican et al. |
| 2011/0144764 A1 | 6/2011 | Bagga et al. |
| 2011/0151400 A1 | 6/2011 | Boiangiu et al. |
| 2011/0172716 A1 | 7/2011 | Glerum |
| 2011/0224675 A1 | 9/2011 | Tofighi et al. |
| 2011/0262554 A1 | 10/2011 | Masinaei et al. |
| 2011/0280924 A1 | 11/2011 | Lin et al. |
| 2012/0053692 A1 | 3/2012 | Voor et al. |
| 2012/0064290 A1 | 3/2012 | Esat et al. |
| 2012/0093895 A1 | 4/2012 | Song et al. |
| 2012/0164187 A1 | 6/2012 | Ollila et al. |
| 2012/0237568 A1 | 9/2012 | Murphy et al. |

(56) References Cited

U.S. PATENT DOCUMENTS

| | | |
|---|---|---|
| 2013/0013071 A1 | 1/2013 | Betz et al. |
| 2013/0059382 A1 | 3/2013 | Tsai et al. |
| 2013/0122057 A1 | 5/2013 | Garigapati et al. |
| 2013/0144376 A1 | 6/2013 | Dave et al. |
| 2013/0145963 A1 | 6/2013 | Cai et al. |
| 2013/0150227 A1 | 6/2013 | Wang et al. |
| 2013/0189338 A1 | 7/2013 | Drapeau et al. |
| 2013/0195805 A1 | 8/2013 | Wei et al. |
| 2013/0202670 A1 | 8/2013 | Darmac et al. |
| 2013/0236513 A1 | 9/2013 | Guelcher et al. |
| 2013/0244942 A1 | 9/2013 | Benedict et al. |
| 2013/0274890 A1 | 10/2013 | McKay |
| 2013/0282138 A1 | 10/2013 | McKay |
| 2013/0297038 A1 | 11/2013 | McKay |
| 2014/0017281 A1 | 1/2014 | Pomrink |
| 2014/0031950 A1 | 1/2014 | Cook et al. |
| 2014/0079753 A1 | 3/2014 | Darby et al. |
| 2014/0170202 A1 | 6/2014 | Peters et al. |
| 2014/0195005 A1 | 7/2014 | McKay |
| 2014/0205674 A1 | 7/2014 | Wei |
| 2014/0212471 A1 | 7/2014 | Drapeau et al. |
| 2014/0222159 A1 | 8/2014 | Bursac et al. |
| 2014/0271779 A1 | 9/2014 | Bagga et al. |
| 2014/0271786 A1 | 9/2014 | Bagga et al. |
| 2014/0271914 A1 | 9/2014 | Wagner |
| 2014/0294913 A1 | 10/2014 | Hasirci et al. |
| 2014/0314822 A1 | 10/2014 | Carter et al. |
| 2015/0010607 A1 | 1/2015 | Francis et al. |

FOREIGN PATENT DOCUMENTS

| | | |
|---|---|---|
| CA | 2027259 C | 12/2000 |
| JP | 2002522148 A | 7/2002 |
| JP | 2009519052 A | 5/2009 |
| WO | 2000009024 | 2/2000 |
| WO | 2003024316 A2 | 3/2003 |
| WO | 2003065996 A2 | 8/2003 |
| WO | 2004105825 A1 | 12/2004 |
| WO | 2005051447 A1 | 6/2005 |
| WO | 2005084701 A1 | 9/2005 |
| WO | 2007067561 A2 | 6/2007 |
| WO | 2008010083 A2 | 1/2008 |
| WO | 2008019024 A1 | 2/2008 |
| WO | 2008032054 A2 | 3/2008 |
| WO | 2010139792 A1 | 12/2010 |
| WO | 2011001028 A1 | 1/2011 |
| WO | 2011058134 A1 | 5/2011 |
| WO | 2011084898 A2 | 7/2011 |
| WO | 2011109581 A1 | 9/2011 |
| WO | 2011109912 A1 | 9/2011 |
| WO | 2014128289 A1 | 8/2014 |

100

200

300 hydration 300                302

400

OR putty (after cap removal)

BIOACTIVE BONE GRAFT SUBSTITUTES

CROSS-REFERENCE TO RELATED APPLICATION

This application is a continuation of U.S. patent application Ser. No. 13/493,531, filed Jun. 11, 2012, which is incorporated by reference herein in its entirety for all purposes.

FIELD OF THE INVENTION

The present invention generally relates to bone graft substitutes that include bioactive glass and a carrier. The invention also relates to implants that include such bone graft substitutes, methods of making and using the bone graft substitutes, and kits that include such bone graft substitutes. Example formulations include bioactive glass, glycerol, and polyethylene glycol. Other formulations include bioactive glass and collagen, and optionally an angiogenic agent, such as hyaluronic acid. Further formulations include bioactive glass, hyaluronic acid, and glycerol.

BACKGROUND OF THE INVENTION

Autograft, i.e., using the patient's own tissue, is considered to be the "gold standard" for bone grafting. However, its use continues to be limited due to donor site pain and morbidity issues. As a result, allograft bone grafting has gained popularity over the years. Issues related to disease transmission and sourcing, however, continue to be a deterrent to the use of allograft products.

Synthetic bone graft substitutes have also been used. Products in the synthetic bone graft substitute area include products that are primarily composed of βTCP or a mix of Hydroxyapatite and βTCP. These products have a variable resorption/degradation profile with hydroxyapatite taking up to years to resorb. Growth factor based products such as rh-BMP2 have also been used for bone grafting but have been associated with adverse events.

All of the above have resulted in the need for better and "safer" bone grafting alternatives. More recently, a class of products called synthetic bioactive bone graft substitutes has been considered.

SUMMARY OF THE INVENTION

The present invention generally relates to bone graft substitutes that include bioactive glass and a synthetic resorbable carrier.

By way of example, bone graft substitute formulations may be provided that include bioactive glass, glycerol and polyethylene glycol. The present bone graft substitute formulations may be provided e.g., in the form of a soft moldable putty, in a powder that may be reconstituted to form a putty, in a flowable, extrudable gel form, or in a crunch form. By way of example, bone graft subtitutes may be provided that include e.g. 71% or more by weight of bioactive glass or les than about 67% by weight of bioactive glass.

Other non-limiting example bone graft substitutes may include collagen and bioactive glass particles, and optionally an angiogenic agent, such as hyaluronic acid. According to these examples, bone graft substitutes may be provided that e.g., include at least about 15% by weight of collagen and at least about 75% by weight of bioactive glass particles. Non-limiting example embodiments may further include an angiogenic agent, such as hyaluronic acid. According to non-limiting example embodiments, such bone graft substitutes may include about 5-20% by weight of Type I Bovine Collagen, about 0.1-10% by weight of an angiogenic agent, and about 80-85% by weight of Bioactive glass particles. These bone graft substitutes may be for example in a form selected from a scaffold, strip and putty/pack.

According to other non-limiting example embodiments, bone graft substitutes may be provided that include bioactive glass, hyaluronic acid, and glycerol. According to non-limiting example embodiments, putty formulations may be formulated having e.g. from about 70% to about 76% by weight of bioactive glass, from about 22% to about 28% by weight of glycerol, and about 1-3% by weight of hyaluronic acid. According to other non-limiting example embodiments, gel formulations may be formulated having e.g. from about 59% to about 66% by weight of bioactive glass, from about 31% to about 39% by weight of glycerol, and about 1% to about 4% by weight of hyaluronic acid. According to further non-limiting example embodiments, crunch formulations may be formulated having e.g. from about 54% to about 60% by weight of bioactive glass, from about 34% to about 40% by weight of glycerol, and about 5% to about 7% by weight of hyaluronic acid.

Further provided are implants that include the present bone graft substitutes, methods of making and using the present bone graft substitutes; and kits that include such bone graft substitutes or implants.

Example methods may include administering a bone graft substitute to a mammal by surgically inserting one or more of the present bone graft substitutes into a mammal. The bone graft substitutes may be administered for example by themselves e.g., in the form of a strip or putty, or the bone graft substitute may be available in conjunction with an implant, such as being incorporated therein or thereon.

Example kits may include for example, any of the present bone graft substitutes or implants that include them, which may be contained in a container or delivery device, such as a syringe; and may further include instructions and/or at least one other additional component for preparing and/or inserting the present bone graft substitutes into a mammal.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings.

DETAILED DESCRIPTION

Figure 1:
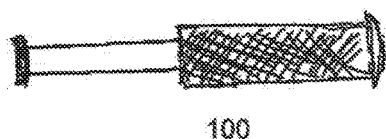
FIG. 1 depicts an example syringe that may be suitable for holding and/or inserting non-limiting example bone graft substitutes according in accordance with example embodiments.

Embodiments of the disclosure are generally directed to synthetic bone graft substitutes that include bioactive glass and a synthetic resorbable carrier; and implants and kits that include the same. Also included are methods of administering the bone graft substitutes to a mammal.

The aspects, advantages and/or other features of example embodiments of the present disclosure will become apparent in view of the following detailed description, taken in conjunction with the accompanying drawings. It should be apparent to those skilled in the art that the described embodiments of the present disclosure provided herein are merely exemplary and illustrative and not limiting. Numerous embodiments of modifications thereof are contemplated as falling within the scope of the present disclosure and equivalents thereto. Unless otherwise noted, technical terms are used according to conventional usage. Any patents and publications mentioned in this specification are indicative of the level of those skilled in the art to which the invention pertains. All publications, patent applications, patents, and other references mentioned herein are incorporated by reference in their entirety.

In describing example embodiments, specific terminology is employed for the sake of clarity. However, the embodiments are not intended to be limited to this specific terminology.

Definitions

As used herein, "a" or "an" may mean one or more. As used herein, "another" may mean at least a second or more. Furthermore, unless otherwise required by context, singular terms include pluralities and plural terms include the singular.

Bioactive glass is a group of surface reactive glass-ceramic biomaterials, which include, but are not limited to "Bioglass®". Bioactive glass may include for example, 45S5 Bioactive glass material, which has the following make up: 45% $SiO_2$, 24.5% $Na_2O$, 24.5% CaO & 6% $P_2O_5$. This material has the ability to produce a bioactive surface layer of hydroxyapatite which facilitates and results in bony fusion. This material also has a very well defined degradation profile of less than 6 months and has a very safe history of usage. Bioactive glass may be present e.g., in the form of bioactive glass particles. The particles may include for example, fibers or other particle sizes or shapes that may be available to those skilled in the art. For example, the 45S5 material may be available as loose particulates (such as table salt), but may also be processed into various forms such as fibers, spherical beads, or micron level forms/shapes (e.g., rods, ribbon shapes, spheres, etc.)

As used herein, the term "mammal" is intended to include any "subject" or "patient" animal, (including, but not limited to humans) to whom the present formulations may be administered. A subject or patient or mammal may or may not be under current medical care, and may or may not have had one or more prior treatments. Although, as would be apparent to those skilled in the art, the formulations and dosages may be different for non-humans than for humans, taking into consideration certain solvent requirements are provided herein for safety for injection.

As used herein, "an effective amount" refers to an amount of the specified constituent in a composition or formulation, or an amount of the overall formulation that is effective in attaining results, the purpose for which the constituent or composition is provided. Therefore, an effective amount of a formulation would be an amount suitable for achieving the desired bone graft effect in a subject, such as a mammal (e.g., human) to which the present formulation is administered.

Numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

As indicated above, provided herein are bone graft substitutes that include bioactive glass and a synthetic resorbable carrier. Bioactive glass, such as 45S5 Bioactive Glass material is in the form of loose particles and handling of this material presents a challenge. Hence, synthetic resorbable carriers have been developed by the present inventors in order to facilitate the handling & delivery of the 45S5 Bioactive Glass material.

BAG, Glycerol and PEG

Non-limiting examples of the present invention may include bone graft substitutes that include bioactive glass, glycerol and polyethylene glycol (PEG). The bioactive glass may be for example in the form of particles, such as fibers. Non-limiting example bioactive glass particles may include Bioglass particles. The glycerol and polyethylene glycol form a carrier, which may according to certain embodiments degrade at a desired rate, e.g., within a matter of days following implantation, to expose the bioactive glass for osteostimulatory bone healing. PEG is commercially available and is known to those skilled in the art.

Non-limiting example bone graft substitute formulations may include about 71% or more by weight of bioactive glass particles, glycerol, and polyethylene glycol. Example embodiments may include about 71% to about 75% by weight of 45S5 bioactive glass, about 15% to about 19% by weight of glycerol, and about 10% to about 14% by weight of polyethylene glycol in a soft, moldable putty form. Further example embodiments may include about 71% by weight of 45S5 bioactive glass, about 17% by weight of glycerol, and about 12% by weight of polyethylene glycol 2000. Further non-limiting example embodiments may include about 73% or more by weight of bioactive glass. Even further example embodiments may include about 77% or more by weight of bioactive glass.

71% by weight of bioactive glass, in itself, is a high percentage (by weight) of material in the formulation. By increasing the percentage even further, the handling of the product is affected adversely. The end product is no longer cohesive and has a tendency to fall apart. Thus, it would be unexpected that formulations having this high amount of bioactive glass would form acceptable compositions. According to non-limiting example embodiments, the bone graft may be in the form of a soft moldable putty. Example putty compositions of bioactive glass bone graft substitutes may advantageously be easily handled by the physician and maintain integrity after the implant until a surgical site is closed and stays in place during irrigation.

Other non-limiting example embodiments of bone graft substitutes may include about 67% or less by weight of bioactive glass, glycerol, and polyethylene glycol. Non-limiting example embodiments may include about 63% to about 67% by weight of 45S5 bioactive glass particles, about 19% to about 23% by weight of glycerol, and about 12% to about 16% by weight of polyethylene glycol. Non-limiting example embodiments include bone graft substitutes that include about 65% by weight of 45S5 bioactive glass particles, about 21% by weight of glycerol, and about 14% by weight of polyethylene glycol 2000. Other non-limiting example embodiments are directed to bone graft substitutes that include about 66% to about 68% by weight of 45S5 bioactive glass, about 17% to about 21% by weight of glycerol, and about 11% to about 15% by weight of polyethylene glycol. For example, embodiments may include about 71% by weight of 45S5 bioactive glass, about 17% by weight of glycerol, and about 12% by weight of polyethylene glycol 2000. In these embodiments, the bone graft substitutes may be present e.g., in a soft, moldable putty form.

As indicated above, the present bone graft substitutes may be for example, in a form selected from a soft moldable putty. They may also be in the form of powder that may be reconstituted to form a soft moldable putty according to methods known to those skilled in the art, a flowable extrudable gel or a crunch form. As indicated above, the 45S5 material may be available as loose particulates or processed into various forms such as fibers, spherical beads, or micron level forms/shapes (e.g., rods, ribbon shapes, spheres, etc.)

Thus, example embodiments may include bone graft substitutes that may be formulated into a flowable, extrudable gel form. By way of non-limiting example embodiments, such bone graft substitutes may include for example about 50% to about 60% by weight of 45S5 bioactive glass, about 22% to about 18% by weight of glycerol, and about 28% to about 22% by weight of polyethylene glycol.

By way of further example of bone graft substitutes that may be formulated into a flowable, extrudable gel, bone graft substitutes may be provided that include from about 53% to about 57% by weight of bioactive glass, such as 45S5 bioactive glass, about 18% to about 22% by weight of glycerol, and about 22% to about 28% by weight of polyethylene glycol. Example embodiments may include about 55% by weight of 45S5 bioactive glass, about 20% by weight of glycerol, and about 25% by weight of polyethylene glycol 2000. Other examples may include from about 52% to about 58% by weight of bioactive glass, about 16% to about 23% by weight of glycerol, and about 22% to about 29% by weight of polyethylene glycol.

Example embodiments may include about 55% by weight of 45S5 bioactive glass, about 18% by weight of glycerol, and about 27% by weight of polyethylene glycol 2000. Further examples may include from about 48% to about 52% by eight of bioactive glass, about 18% to about 22% by weight of glycerol, and about 28% to about 32% by weight of polyethylene glycol. Thus, example embodiments may include about 50% by weight of 45S5 bioactive glass, about 20% by weight of glycerol, and about 30% by weight of polyethylene glycol 2000.

Other non-limiting example bone graft substitutes that may be e.g., in a crunch form, may include about 40% to about 67%, by weight of bioactive glass, such as 45S5 bioactive glass, about 12% to about 36% by weight of glycerol and about 12% to about 38% by weight of polyethylene glycol. Further embodiments may include about 48% to about 52%, by weight of bioactive glass, such as 45S5 bioactive glass, about 13% to about 17% by weight of glycerol and about 33% to about 37% by weight of polyethylene glycol. By way of non-limiting example, a crunch formulation may include e.g., about 50%, by weight of bioactive glass, such as 45S5 bioactive glass, about 15% by weight of glycerol and about 35% by weight of polyethylene glycol.

Thus, non-limiting example formulations may include any of the following:

|  | Bioactive Glass | Glycerol | PEG 2000 |
| --- | --- | --- | --- |
| Putty | 71% | 17% | 12% |
| Gel | 55% | 20% | 25% |
| Crunch | 50% | 15% | 35% |

According to non-limiting example embodiments, bone graft substitutes are provided that may include bioactive glass, glycerol and polyethylene glycol, which do not include collagen, or which contain only negligible amounts of collagen.

The following are some of the possible advantages of using one or more of the present bone graft substitute formulations that include bioactive glass particles, glycerol and polyethylene glycol: The present formulations may be osteostimulative as soon as they are implanted into a mammal (i.e., activating chemistry promotes bone formation). The present formulations may act to signal genetic pathways, attract cells, and increase the rate of proliferation and bone formation. Certain of the present formulations may provide a high bioactive glass content in a flowable putty, which may be clearly visible on X-ray (radiopaque). The bone graft substitutes may have advantageously have antimicrobial properties. The bone graft substitutes may be formulated into user friendly forms like extrudable gel (for MIS applications) and crunch (provides a 3D scaffold for cell attachment and proliferation). The present formulations may have exceptional handling (i.e., will not migrate and do not fall apart on irrigation and do not stick to gloves, for example of a surgeon inserting the bone graft substitute to a mammal.

BAG and Collagen

Other example bone graft substitutes may include collagen and bioactive glass, and optionally an angiogenic agent. As with other embodiments herein, the bioactive glass may be for example in the form of particles, such as fibers. Non-limiting example bioactive glass particles may include Bioglass particles. The collagen may be determined by those skilled in the art, but should be a suitable form of collagen for insertion into a mammal. By way of non-limiting example the collagen may be Type I Bovine Collagen.

According to these examples, bone graft substitutes may be provided that e.g., include at least about 15% by weight of collagen and at least about 75% by weight of bioactive glass, such as Bioglass particles. According to further example embodiments, the bone graft substitute may include at least about 17% by weight of collagen.

The bone graft substitutes that include collagen and bioactive glass particles may be for example in a form selected from a scaffold, strip and putty/pack. For example the bone graft substitute may be in a putty formulation or it may be in a dry (e.g., powder) form, which may become a putty upon hydration e.g., by someone who is preparing the bone graft substitute for insertion into a mammal.

The strip version of this graft is intended to remain compression resistant following hydration and serve as a semi-rigid bone graft scaffold e.g., for posterolateral fusion. In order to maintain these properties, the following composition may be used: about 20% by weight of collagen and about 80% by weight of bioactive glass particles.

According to non-limiting example embodiments, bone graft substitutes may include about 17-23% by weight of collagen, and about 77-83% by weight of bioactive glass particles. Other non-limiting examples may include about 18-22% by weight of collagen, and about 78-82% by weight bioactive glass, such as Bioglass particles. According to example embodiments, bone graft substitutes may be provided that include collagen and bioactive glass particles, for example in an amount of about 20% by weight of collagen and about 80% by weight of bioactive glass particles.

Current available products typically consist of collagen, calcium based ceramics, and recently the addition of bioactive glass. However, the bioactive component is relatively low (15%) and therefore, does not achieve a desired, maximized enhanced in vivo apatite formation that is provided by this material. The present formulations may remove the calcium ceramic component, and increase the bioactive glass component of the collagen based scaffold to maximize the in vivo bioactivity of the graft. The collagen processing will be done such that the graft remains as a semi-rigid scaffold that can hydrate with blood and bone marrow but retains a porosity ideal for bone growth (150-450 µm). The porosity of resulting bone graft formulations may be e.g. 150-450 µm. The removal of the calcium ceramic allows for a higher composition of bioactive glass particles, enhancing both the bioactive and osteostimulatory effect.

According to non-limiting example embodiments of bone graft substitutes that include collagen and bioactive glass particles, such bone graft substitute formulations do not include calcium ceramic, or only include negligible amounts of calcium ceramic.

Additionally, there is an intended putty/pack formulation that may appear similar in a dry state but become moldable when hydrated. The putty formulations may advantageously maximize in vivo bioactivity, and osteostimulatory effect.

In order to further enhance the bone formation capabilities of the graft, the incorporation of hyaluronic acid can be included. The value of this component is as an angiogenic agent, helping to kick start the healing process by inducing the formation of new blood supply to the wound site. By introducing a small amount, the graft would be able to maintain its structural properties while adding the benefit of the angiogenic agent.

Thus, non-limiting example embodiments of a putty/pack formulation that include collagen and bioactive glass particles may further include at least one angiogenic agent. The angiogenic agent may include e.g., one or more polysaccharides, such as hyaluronic acid (glycosaminoglycan) or other angiogenic agents known to those skilled in the art.

According to non-limiting example embodiments, bone graft substitutes having an angiogenic agent may include for example about 5-20% by weight of collagen, such as Type I Bovine Collagen, about 0.1-10% by weight of an angiogenic agent (such as hyaluronic acid (HLA)), and about 80-85% by weight of bioactive glass, such as Bioglass particles. According to other example embodiments, bone graft substitutes may include about 15-20% by weight of collagen, such as Type I Bovine Collagen, about 1-5% by weight of an angiogenic agent, and about 80% by weight of bioactive glass, such as Bioglass particles. Other examples may include about 17-22% by weight of collagen, about 1-5% by weight of an angiogenic agent, and about 78%-82% by weight of bioactive glass.

Non-limiting example formulations may include any of the following:

|  | Bioactive Glass | Collagen | Hyaluronic Acid |
| --- | --- | --- | --- |
| Strip | 80% | 19.75% | 0.25% |
| Strip | 80% | 19% | 1% |
| Putty | 80% | 16% | 4% |
| Putty | 84% | 8% | 8% |

The present bone graft substitute formulations may be advantageous in a variety of ways. For example, the bone graft substitute may be osteostimulative as soon as it is implanted into a mammal (activating chemistry promotes bone formation). The formulations may also signal genetic pathways, attract cells, and increase the rate of proliferation and bone formation. The present formulations also provide the highest bioglass content in a collagen-based scaffold. This is clearly visible on X-ray (radiopaque). The present formulations also provide antimicrobial properties; have angiogenic potential (hyaluronic acid component), and may be compression resistant for posterolateral grafting.

Bioactive Glass, Hyaluronic Acid and Glycerol

According to other non-limiting example embodiments, bone graft substitutes may be provided that include bioactive glass, hyaluronic acid, and glycerol. The bioactive glass may be as set forth herein, and may be for example 45S5 bioactive glass particles.

Such formulations may by in the form of a putty, gel, or crunch formulation. According to non-limiting example embodiments, putty formulations may be formulated having e.g. from about 70% to about 76% by weight of bioactive glass, from about 22% to about 28% by weight of glycerol, and about 1-3% by weight of hyaluronic acid. According to other non-limiting example embodiments, gel formulations may be formulated having e.g. from about 59% to about 66% by weight of bioactive glass, from about 31% to about 39% by weight of glycerol, and about 1% to about 4% by weight of hyaluronic acid. According to further non-limiting example embodiments, crunch formulations may be formulated having e.g. from about 54% to about 60% by weight of bioactive glass, from about 34% to about 40% by weight of glycerol, and about 5-7% by weight of hyaluronic acid.

By way of further example, non-limiting example formulations may include any of the following formulations:

|  | Bioactive Glass | Glycerol | Hyaluronic Acid |
| --- | --- | --- | --- |
| Putty | 71% | 27% | 2% |
| Gel | 60% | 37%-38% | 2%-3% |
| Crunch | 55% | 39% | 6% |
| Putty | 75% | 23% | 2% |
| Gel | 65% | 32%-33% | 2%-3% |
| Crunch | 59% | 35% | 6% |

Example bone graft substitutes may further include one or more excipients and/or additives that may be selected, for example based on the type of composition being formed, desired route of administration and properties to be achieved, etc. The excipients should be selected so as not to disadvantageously alter the required or desired physical characteristics of the bone graft substitute.

By way of non limiting example, the additive may include one or more antiviricides, such as those effective against HIV and hepatitis; antimicrobial and/or antibiotics such as erythromycin, bacitracin, neomycin, penicillin, polymyxin B, tetracycline, viomycin, chloromycetin and streptomycin, cefazolin, ampicillin, azactam, tobramycin, clindamycin and gentamycin.

By way of further example, the additive may include cellular material additive taken from a group consisting of living cells and cell elements such as chondrocytes, red blood cells, white blood cells, platelets, blood plasma, bone marrow cells, mesenchymal stem cells, pluripotential cells, osteoblasts, osteoclasts, and fibroblasts, epithelial cells, and endothelial cells.

It is also envisioned that other additives which can be added to the composition are amino acids, peptides, vitamins, co-factors for protein synthesis; hormones; endocrine tissue or tissue fragments; synthesizers; enzymes such as collagenase, peptidases, oxidases; polymer cell scaffolds with parenchymal cells; angiogenic drugs and polymeric carriers containing such drugs; collagen lattices; biocompatible surface active agents, antigenic agents; cytoskeletal agents; cartilage fragments.

Formable compositions may be used to correct surgical defects that may be caused by trauma, pathological disease, surgical intervention or other situations where defects need to be managed in osseous surgery. It may be important or advantageous to have the defect filler in the form of a stable, viscous formable composition to facilitate the placement of the composition into the surgical site, which is usually uneven in shape and depth. The surgeon may take the composition on a spatula or other instrument and trowel it into the site or take it in his/her fingers to shape the bone defect material into the proper configuration to fit the site being corrected. It is also important that the defect filler be biocompatible.

Surgical implants and compositions should be designed to be biocompatible in order to successfully perform their intended function. Biocompatibility may be defined as the characteristic of an implant or composition acting in such a way as to allow its therapeutic function to be manifested without secondary adverse affects such as toxicity, foreign body reaction or cellular disruption. To help avoid adverse reaction, example bone graft substitutes may be prepared in sterile formulations for implantation into a mammal.

Implants that Include the Bone Graft Substitutes

Also provided herein are implants that may include one or more of the present bone graft substitutes. For example, the present bone graft substitutes may be used as a graft within or inside interbody spacers or for treatment of compression fractures.

Methods of Making the Bone Graft Substitutes

Further provided are methods of making the present bone graft substitutes. The methods may depend for example based on the final desired formulation. Example methods may include for example, melting PEG, adding glycerol and thereafter adding bioactive glass. According to other embodiments, example methods may include mixing hyaluronic acid in glycerol and thereafter adding bioactive glass. Further example methods may include swelling collagen in acid, mixing bioactive glass and freezing.

Methods of Inserting the Bone Graft Substitutes

Also provided herein are methods that include inserting the present bone graft substitutes into a mammal in need thereof. Example methods may include administering a bone graft substitute to a mammal, e.g., by surgically inserting one or more of the present bone graft substitutes into a mammal, such as a mammal in need thereof. The bone graft substitutes may be administered for example by themselves e.g., in the form of a strip or putty, or the bone graft substitute may be available in conjunction with an implant, e.g., as a coating on the implant or incorporated therein or thereon.

As previously indicated, the subject may be a mammal (as well as other animals), and the mammal may be (but does not have to be) human.

Embodiments of the present invention may include moldable and shapeable putty compositions that may be used for example to fill bone defects.

Kits that Include the Bone Graft Substitutes

Also provided herein are kits that include one or more of the present bone graft substitutes. The bone graft substitute may be provided for example in the kit in an already formulated form, e.g., in the form of a strip. Alternatively, the bone graft substitute may be provided in a form that may be reconstituted or otherwise formed into a bone graft substitute, such as in a powder form that may be hydrated to form a putty. Alternatively the bone graft substitute may be provided in or on an implant.

Example kits may include for example, any of the present bone graft substitutes, along with at least one additional component that may be used for example in the storage, preparation or use of the bone graft substitutes. According to example embodiments, the additional component may include instructions for the preparation of the bone graft substitute, instructions for the use of the bone graft substitute, a tool for insertion of the bone graft substitute into a mammal, a tool or vehicle for hydration of a dry form of the bone graft substitute, and/or an implant to be inserted into the mammal with the bone graft substitute. For example, the bone graft substitute may be provided in a syringe for reconstitution and/or administration to a patient. According to example embodiments, products may be provided in a syringe with an attachment to deliver product in a minimally invasive manner. Other possible ingredients in kits may include disposal implements or treatment literature.

The following examples are provided to further illustrate various non-limiting embodiments and techniques encompassed by the present invention. It should be understood, however, that these examples are meant to be illustrative and do not limit the scope of the claims. As would be apparent to skilled artisans, many variations and modifications are intended to be encompassed within the spirit and scope of the present disclosure.

EXAMPLES

Example 1

According to non-limiting example embodiments, the present bone graft substitutes may be formulations comprising either BAG, glycerol, and PEG; or BAG, glycerol, and hyaluronic acid. Such products may be in the form e.g., of a moldable putty or moldable doughy crunch putty, which is present inside an administration device, such as a syringe 100, as depicted for example in FIG. 1.

Figure 2:
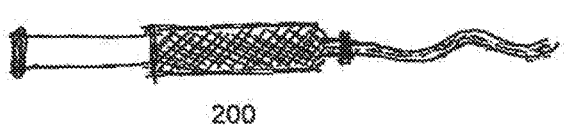
FIG. 2 depicts an example syringe that may be suitable for holding and/or inserting other non-limiting example bone graft substitutes according in accordance with example embodiments.

According to other non-limiting example embodiments, the present bone graft substitutes may be formulations comprising either BAG, glycerol, and PEG; or BAG, glycerol, and hyaluronic acid in the form of an extrudable gel, which may be present e.g., in an administration device, such as a syringe 200, as depicted for example in FIG. 2.

Figure 3:
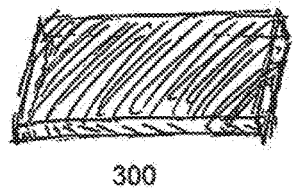
FIG. 3 depicts an example compression resistant strip of example bone graft substitutes according in accordance with example embodiments.
Figure 4:
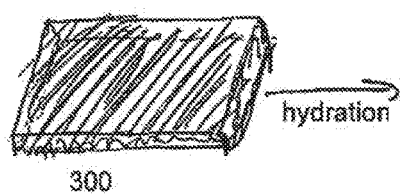
FIG. 4 depicts an example compression resistant strip of example bone graft substitutes that may be formed into a moldable putty upon hydration, according in accordance with example embodiments.
Figure 4:

According to further non-limiting example embodiments, the present bone graft substitutes may be formulations that include collagen and BAG; or collagen, BAG, and hyaluronic acid in the form of compression resistant strip 300 for example as depicted for example in FIG. 3. The compression resistant strip 300 may be formulated such that upon hydration it may turn into a doughy, moldable putty 302 for example as shown in FIG. 4.

Figure 5:
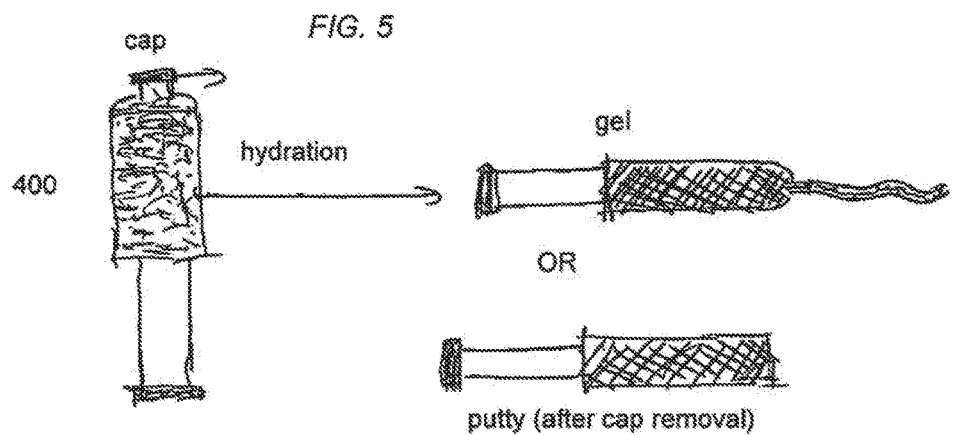
FIG. 5 depicts an example container for example bone graft substitutes that may be formed into a gel or putty upon hydration, according in accordance with example embodiments.

According to further embodiments, bone graft substitutes such as collagen, and BAG; or collagen, BAG, and hyaluronic acid may be included in a container 400 that may include for example, a port for the addition of saline or BMA, or may include a threaded cap 402 as depicted e.g., in FIG. 5. Upon hydration the bone graft substitute may be administered from the container in the form of a gel or in the form of a putty. In embodiments in which the container has a cap, a putty may be administered for example when the cap is removed.

While it is apparent that the invention disclosed herein is well calculated to fulfill the objects stated above, it will be appreciated that numerous modifications and embodiments may be devised by those skilled in the art.

What is claimed is:

1. A method of making a bone graft substitute, the method comprising:

providing a bone graft substitute in a dry form, the bone graft substitute comprising a carrier in the form of a semi-rigid collagen-based scaffold comprising 5-20% by weight of collagen and 0.1-10% by weight of an angiogenic agent, wherein the carrier is free of glycerol and polyethylene glycol, and 84% by weight of bioactive glass particles; and hydrating the dry form of the bone graft substitute to form a moldable putty, wherein the bone graft substitute retains a porosity of 150 to 405 μm when hydrated.

2. The method of claim 1, wherein the angiogenic agent comprises one or more polysaccharides.

3. The method of claim 1, wherein the angiogenic agent comprises hyaluronic acid.

4. The method of claim 1, wherein the collagen is type I bovine collagen.

5. The method of claim 1, wherein the bone graft substitute is free of a calcium ceramic component.

6. The method of claim 1, wherein the angiogenic agent is present at 1-5% by weight.

7. The method of claim 1, wherein the bioactive glass includes 45% $SiO_2$, 24.5% $Na_2O$, 24.5% CaO, and 6% $P_2O_5$.

8. The method of claim 1, wherein the bioactive glass particles include fibers.

9. The method of claim 1, wherein the bone graft substitute is hydrated with a cellular material.

10. The method of claim 9, wherein the cellular material is selected from red blood cells, white blood cells, platelets, blood plasma, and/or bone marrow cells.

11. The method of claim 1, wherein once hydrated, the bone graft substitute is in the form of a stable, viscous formable composition configured to facilitate placement of the bone graft substitute at a surgical site.

12. A method of making a bone graft substitute, the method comprising:

providing a bone graft substitute consisting of a mixture of 17-20% by weight of type I bovine collagen, 1-5% by weight of hyaluronic acid, and 84% by weight of bioactive glass particles, wherein the bone graft substitute is provided in a dry form; and hydrating the dry form of the bone graft substitute to form a moldable putty.

13. The method of claim 12, wherein the bone graft substitute is hydrated with a cellular material.

14. The method of claim 12, wherein before hydration, the bone graft substitute is a compression resistant strip.

15. A method of making a bone graft substitute, the method comprising:

providing a bone graft substitute consisting of a mixture of a carrier and bioactive glass particles, the carrier being in the form of a semi-rigid collagen-based scaffold having 8% by weight of collagen and 8% by weight of hyaluronic acid, and 84% by weight of the bioactive glass particles, wherein the bone graft substitute is provided in a dry form; and hydrating the dry form of the bone graft substitute to form a moldable putty.

16. The method of claim 15, wherein the bone graft substitute is hydrated with a cellular material.

17. The method of claim 15, wherein the bioactive glass particles include fibers.

18. The method of claim 15, wherein the bone graft substitute is a compression resistant strip before hydration.

* * * * *